United States Patent [19]

Grotenhuis et al.

[11] Patent Number: 4,933,499

[45] Date of Patent: Jun. 12, 1990

[54] PROCESS FOR PURIFICATION OF ALKENYL AROMATIC COMPOUNDS CONTAINING A BENZALDEHYDE IMPURITY

[75] Inventors: Paul A. M. Grotenhuis; Brian L. Goodall, both of Amsterdam, Netherlands

[73] Assignee: Shell Oil Company, Houston, Tex.

[21] Appl. No.: 315,744

[22] Filed: Feb. 27, 1989

[30] Foreign Application Priority Data

Feb. 29, 1988 [GB] United Kingdom ............... 8804725

[51] Int. Cl.$^5$ .................. C07C 45/90; C07C 7/00
[52] U.S. Cl. .................... 568/438; 585/808; 585/802; 585/809; 585/654; 568/435
[58] Field of Search ............... 568/438; 585/435, 808, 585/802, 809, 654

[56] References Cited

U.S. PATENT DOCUMENTS

| | | | |
|---|---|---|---|
| 2,544,562 | 3/1951 | Michael | 568/438 |
| 2,897,238 | 7/1959 | Toppel | 568/438 |
| 3,816,478 | 6/1974 | Washall et al. | 549/542 |
| 4,277,626 | 7/1981 | Forss et al. | 568/438 |
| 4,691,034 | 9/1987 | Sanderson et al. | 549/542 |

*Primary Examiner*—Werren B. Lone

[57] ABSTRACT

The invention relates to a process for the purification of alkenyl aromatic compounds which contain benzaldehyde as an impurity. This process comprises steps for contacting a benaldehyde-containing alkenyl aromatic compound with a bisulphite treating agent, and separating the resulting benzaldehyde-bisulphite addition product from the alkenyl aromatic compound. In certain preferred embodiments, the treating agent is a modified anion-exchange resin containing bound bisulphite ions. Optionally, the process then further comprises a step for recovering the benzaldehyde from the resin addition product by contact with an aqueous sodium carbonate solution or by steam distillation.

9 Claims, No Drawings

PROCESS FOR PURIFICATION OF ALKENYL AROMATIC COMPOUNDS CONTAINING A BENZALDEHYDE IMPURITY

The invention relates to a process for purification of alkenyl aromatic compounds, for example styrene, and more particularly to a process for the treatment of alkenyl aromatic compounds to remove benzaldehyde impurities.

Styrene is commonly produced by dehydration of methylphenylcarbinol. In a process of particular interest, styrene is produced in a sequence of three reaction steps, the last of which involves dehydration of methylphenylcarbinol:

step I: peroxidation of ethylbenzene with oxygen to ethylbenzene hydroperoxide (EBHP)

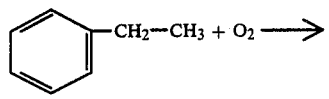

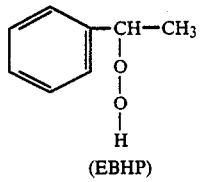

(EBHP)

step II: epoxidation of propylene with EBHP to propylene oxide (PO) and methylphenylcarbinol (MPC)

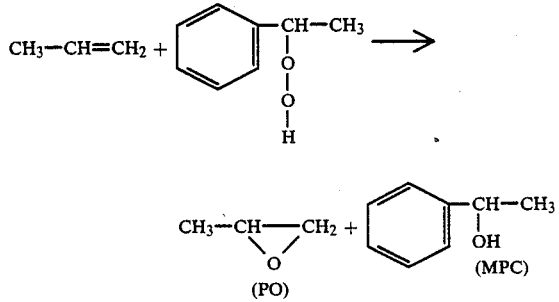

step III: dehydration of methylphenylcarbinol to styrene and water

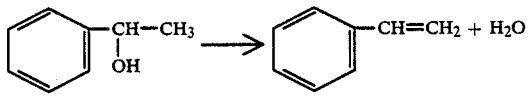

Benzaldehyde is produced as a byproduct in such processes. Separation of the benzaldehyde from the styrene accomplishes both the recovery of a valuable benzaldehyde product and the improvement of the styrene product quality.

The styrene may be purified and the benzaldehyde recovered by distillation. However, distillation may result in an undesirable polymerization of the styrene and require use of polymerization inhibitors. Furthermore distillative separation is not complete and the separated benzaldehyde contains traces of styrene.

In the particular case of styrene production and purification, it has been found that benzaldehyde removal can be accomplished without such disadvantages by contacting the impure styrene with a bisulfite containing treating agent and separating the bisulphite-benzaldehyde addition product from the styrene.

More generally, it has been found that alkenyl aromatic compounds, containing benzaldehyde impurities, are purified by removal therefrom of benzaldehyde in a process which comprises steps for contacting the benzaldehyde-containing alkenyl aromatic compound with a bisulphite treating agent, and separating from the alkenyl aromatic compound the obtained benzaldehyde-bisulphite addition product.

The alkenyl aromatic compounds which may be purified under practice of the invention include styrene and substituted styrenes, having alkyl substitution in either the aromatic ring or in the alkenyl group. Preferably, the invention is applied to the treatment of a material wherein the alkenyl aromatic compounds consist essentially of styrene.

In one embodiment of the invention, the bisulphite agent is a bisulfite compound, preferably an alkali bisulphite or ammonium bisulphite. Sodium bisulphite is the more preferred agent.

For contact with the alkenyl aromatic compounds, the bisulfite treating agent may be applied in the form of a solid salt, or in the form of a liquid solution, for instance, a solution in water or another solvent, preferably a solvent essentially immiscible with the alkenyl aromatic compound. In such embodiments, the bisulfite-benzaldehyde addition product is readily separated from the alkenyl aromatic by physical means.

In certain preferred embodiments, the bisulphite agent is applied in the form of bisulfite ions bound to an anion exchange resin. The anion exchange resin contains exchangeable anions, which are bound to a matrix by basic binding groups.

In order to prepare a modified anion exchange resin, containing bound bisulphite ions, the anion of the anion exchange resin is exchanged for the bisulphite anion. For this purpose the anion exchange resin may be contacted with an aqueous solution of bisulphite, preferably sodium bisulphite.

The anion exchange resin for this service is not critical to the invention. The common resins, which have a matrix which is composed of polystyrene, aliphatic polyamine resin, mixed polyalkylene amines or styrene-divinylbenzene copolymers, are very suitable. Examples of suitable anion exchange resins are described in Ullmanns Encyclopädie der technischen Chemie, fourth edition, 1977, Part 13, particularly at pages 301–303.

Specific examples of suitable anion exchange resins include strongly basic resins such as styrene-divinylbenzene copolymers with anion exchange groups $\phi-CH_2N^+(CH_3)_3Cl^-$, strongly basic styrene-divinlybenzene copolymers with anion exchange groups $\phi-CH_2N^+(CH_3)_2(C_2H_4OH)Cl^-$, strongly basic styrene-divinylbenzene copolymers with anion exchange groups $\phi-CH_2S^+(CH_3)_2Cl^-$, weakly basic styrene-divinylbenzene copolymers with anion exchange groups $\phi-CH_2NHC_2H_4NHC_2H_4NH_2$, wherein $\phi$ is an aromatic ring of the matrix.

One suitable method for preparing a modified anion exchange resin for use as a bisulfite treating agent for this invention involves contacting the resin with an aqueous sodium bisulphite solution and washing the resulting resin with demineralized water and then with ethanol and pentane.

Styrene (or other alkenyl aromatic compound) contaminated with benzaldehyde is contacted with the bisulfite-ion containing modified exchange resin, preferably in a fixed bed. Benzaldehyde is trapped on the solid resin as a benzaldehyde-bisulfite addition product from which the liquid alkenyl aromatic compound is readily separated by draining, settling or other physical means.

The separated benzaldehyde, trapped on the modified anion exchange resin, can be released by contacting the benzaldehyde-containing resin by further ion exchange, for example, with an aqueous solution of sodium carbonate. The benzaldehyde released may be separated and distilled to obtain substantially pure benzaldehyde. The anion-exchange resin may be regenerated for reuse by re-exchange with a source of bisulphite ion, e.g. a sodium bisulphite solution.

Alternatively the benzaldehyde can be recovered directly from the modified resin by the use of steam distillation. The benzaldehyde may than be separated from the distillate by phase separation.

EXAMPLE 1

20 g of the anion exchange resin Amberlist IRA-400 (Amberlist is a registered trademark) were added to a solution of 10 g of sodium metabisulphite in 60 g of water and the mixture was stirred for one hour at 20° C. The modified solid anion exchange resin, containing bisulphite was filtered off and washed with water and subsequently with ethanol and pentane. A dry resin was obtained.

This modified resin, containing $HSO_3^-$ anions, was introduced into a vertical glass tube and then contacted with 35 g of styrene containing 1% by weight of benzaldehyde. The eluent, exiting the bottom of the tube, did not contain a detectable level of benzaldehyde (determined by gas chromatography).

The resin bed was drained, rinsed with ethanol, and then rinsed with an aqueous sodium carbonate solution. The eluent from the bed contained the benzaldehyde, free from styrene.

EXAMPLE 2

70 g of anion exchange resin Amberlist-400 were added to a solution of 30 g of sodium metabisulphite in 200 g of water and the mixture was stirred for one hour at room temperature. The modified solid anion exchange resin, containing bisulphite, was filtered off and washed with water, ethanol and pentane, respectively. A dry resin was obtained.

The modified anion exchange resin, containing $HSO_3^-$ anions, was introduced into a vertical glass tube and 62 g of impure styrene containing 11.5% by weight of benzaldehyde, calculate on the basis of the total weight of benzaldehyde and styrene, weight, as conducted through the resin bed. The eluent, leaving the bottom of the tube, did not contain a detectable level of benzaldehyde (determined by gas chromatography).

The resin bed was drained, rinsed with ethanol and then with an aqueous sodium carbonate solution in order to release the benzaldehyde. The eluent contained the benzaldehyde, essentially free of styrene.

We claim as our invention:

1. In a process for the preparation of styrene which comprises steps for peroxidizing ethylbenzene with oxygen to produce ethylbenzene, epoxidizing propylene with the ethylbenzene hydroperoxide to coproduce propylene oxide and methylphenylcarbinol, dehydrating the methylphenylcarbinol to produce a crude styrene product containing benzaldehyde impurities, and treating the crude styrene product to separate and recover the benzaldhyde therefrom, the improvement which comprises steps for
   contacting the benzaldehyde-containing crude styrene product in liquid form with one or more bisulfite treating agents selected from the group consisting of alkali metal bisulfites, ammonium bisulfite, and anion exchange resins containing bound bisulfite ions, to form a benzaldehyde-bisulfite addition-product, and
   separating the benzaldehyde-bisulfite addition product from the styrene product.

2. The process of claim 1, wherein the treating agent is sodium bisulphite.

3. In a process for the preparation of styrene which comprises steps for peroxidizing ethylbenzene with oxygen to produce ethylbenzene, epoxidizing propylene with the ethylbenzene hydroperoxide to coproduce propylene oxide and methylphenylcarbinol, dehydrating the methylphenylcarbinol to produce a crude styrene product containing benzaldehyde impurities, and treating the crude styrene product to separate and recover the benzaldehyde therefrom, the improvement which comprises steps for
   contacting the benzaldehyde-containing crude styrene product in liquid form with an anion exchange resin containing bound bisulfite ions, to obtain a benzaldehyde-containing resin addition product, and
   separating the benzaldehyde-containing resin addition product from the styrene product.

4. The process of claim 3, wherein the modified anion-exchange resin is obtained by exchange of bisulfite ions with exchangeable anions of the resin matrix which are bound to the matrix by basic groups.

5. The process of claim 4, wherein the bisulfite-containing anion-exchange resin has been obtained by contact of an anion-exchange resin with an aqueous solution of sodium bisulphite.

6. The process of claim 3, wherein the process further comprises a step for releasing the benzaldehyde from the resin addition product by contacting the resin addition product with an aqueous sodium carbonate solution.

7. The process of claim 3, wherein the process further comprises a step for releasing the benzaldehyde from the resin addition product by steam distillation.

8. The process of claim 4, wherein the process further comprises a step for releasing the benzaldehyde from the resin addition product by contacting the resin addition product with an aqueous sodium carbonate solution.

9. The process of claim 4, wherein the process further comprises a step for releasing the benzaldehyde from the resin addition product by steam distillation.

* * * * *